United States Patent
Husar et al.

(10) Patent No.: US 7,485,263 B2
(45) Date of Patent: Feb. 3, 2009

(54) MICROPROPORTIONING SYSTEM

(75) Inventors: Dieter Husar, Hamburg (DE); Rüdiger Huhn, Hamburg (DE)

(73) Assignee: Eppendorf AG, Hamburg (DE)

( * ) Notice: Subject to any disclaimer, the term of this patent is extended or adjusted under 35 U.S.C. 154(b) by 965 days.

(21) Appl. No.: 10/790,165

(22) Filed: Mar. 1, 2004

(65) Prior Publication Data

US 2004/0166028 A1    Aug. 26, 2004

Related U.S. Application Data

(63) Continuation of application No. 09/486,531, filed on May 22, 2000, now abandoned.

(51) Int. Cl.
*B01L 3/02* (2006.01)
*B01L 3/11* (2006.01)
(52) U.S. Cl. .............. 422/100; 422/103; 422/105; 422/108; 422/106; 73/863.32; 73/864; 73/864.02; 73/864.11; 73/864.34
(58) Field of Classification Search .............. 422/100, 422/103, 105–106, 108; 73/863.25, 863.32, 73/864, 864.02, 864.11, 864.14, 864.34
See application file for complete search history.

(56) References Cited

U.S. PATENT DOCUMENTS

| | | | | |
|---|---|---|---|---|
| 5,085,562 A | * | 2/1992 | van Lintel | 417/413.3 |
| 5,096,388 A | * | 3/1992 | Weinberg | 417/413.3 |
| 5,190,522 A | * | 3/1993 | Wojcicki et al. | 604/65 |
| 5,205,819 A | * | 4/1993 | Ross et al. | 604/67 |
| 5,224,843 A | * | 7/1993 | van Lintel | 417/413.2 |
| 5,271,724 A | * | 12/1993 | van Lintel | 417/413.2 |
| 5,277,556 A | * | 1/1994 | van Lintel | 417/413.2 |
| 5,336,062 A | * | 8/1994 | Richter | 417/413.2 |
| 5,529,465 A | * | 6/1996 | Zengerle et al. | 417/413.2 |
| 5,593,290 A | * | 1/1997 | Greisch et al. | 417/478 |
| 5,759,014 A | * | 6/1998 | Van Lintel | 417/413.3 |
| 6,109,889 A | * | 8/2000 | Zengerle et al. | 417/413.2 |

* cited by examiner

*Primary Examiner*—Brian R. Gordon
(74) *Attorney, Agent, or Firm*—Abelman, Frayne & Schwab

(57) ABSTRACT

A microproportioning system includes a reservoir, a micro-diaphragm pump the entrance of which is connected to the reservoir, an open-jet proportioner the entrance of which is connected to the exit of the micro-diaphragm pump, a proportioning port connected to the exit of the open-jet proportioner, and a proportioning control which is in an operative communication with the micro-diaphragm pump and the open-jet proportioner

17 Claims, 12 Drawing Sheets

Fig. 19
Fig. 20
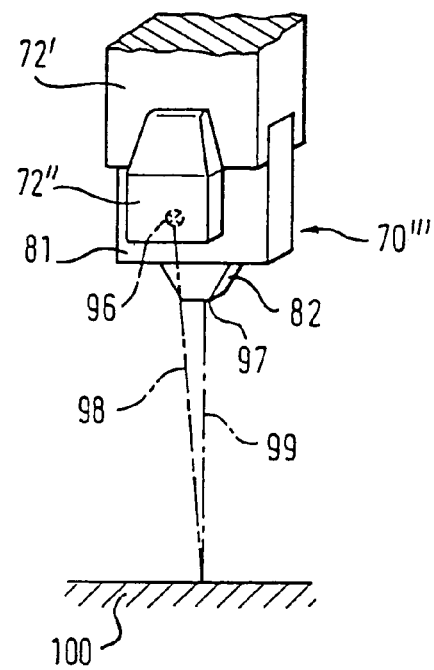
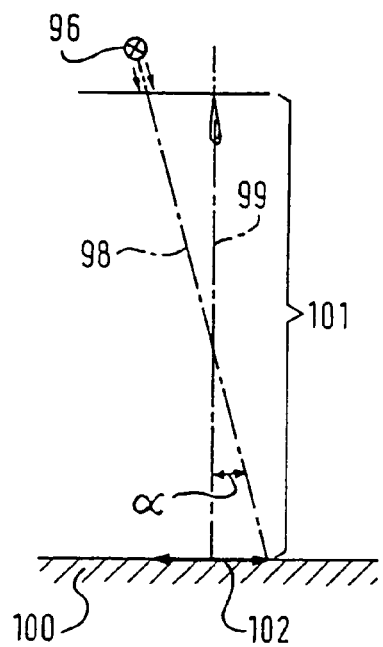
Fig. 21
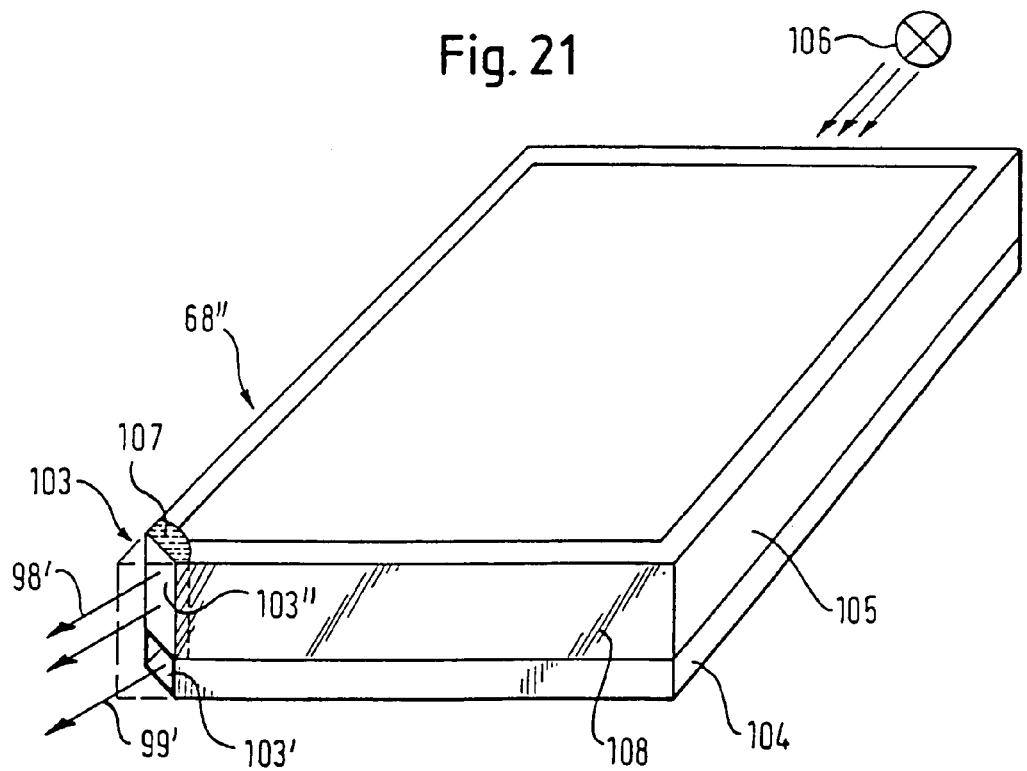

MICROPROPORTIONING SYSTEM

RELATED APPLICATION

This application is a continuation of application Ser. No. 09/486,531 filed May 22, 2000, now abandoned.

BACKGROUND OF THE INVENTION

1. Field of the Invention

The invention relates to a microproportioning system for proportioning liquid volumes in the range of about one nanoliter to a few nanoliters.

2. Description of the Prior Art

In the proportioning systems which are known, a rough distinction is made between pipettes, dispensers, and multi-functional proportioners. All of the three groups are adapted to operate according to two different physical principles: The liquid proportioning process is either brought about by an air cushion or a direct displacement of the liquid takes place with no air cushion interposed. Further, a distinction is made from fixed-volume pipettes having an adjustable volume. The volumes being proportioned are between 0.5 µl and 2.500 µl.

Piston pipettes may be designed as fixed-volume pipettes or adjustable pipettes and operate in a volume range smaller than 1 µl up to 10 µl. The sample is drawn into a plastic syringe where it is separated by an air cushion from the piston in the pipette. Since the weight of the liquid column "is suspended" from the air cushion a pipette error will arise, which requires correction.

Pipettes or dispensers operating according to the direct-displacement principle do not exhibit these errors. They are specifically used in proportioning liquid at high steam pressures, high viscosities, high densities, and in molecular biology—e.g. in the polymerase chain reaction. They have tips or syringes with an integrated piston, which is coupled to a pipette driving means.

Multi-channel pipettes, dispensers, and electronic proportioning systems operate according to the aforementioned principles. Multi-channel pipettes may significantly reduce the number of required pipetting processes by several identical proportioning procedures. This is also the case for dispensers which stepwise dispense a liquid volume received and which also exist in a multi-channel design. Electronic pipettes and proportioning systems permit pipettings at a high reproducibility and have a wide field of application because of the dispensing function integrated. They operate in a volume range from 1 µl to 50 µl.

A precise, simple and low-cost proportioning of smaller liquid volumes would be desirable. Chemical analyses could then be made more precisely, more rapidly and at a lower cost, the latter also being made because of the lower consumption of media. This could enable novel routine diagnoses, e.g. in the field of medical care, or in environmental protection, which have been difficult to realize or have been too expensive hitherto. For applications in the field of biotechnology (e.g. in gene sequencing and genomic analysis) the informative content of examinations could be increased by an improvement of the proportioning quality. A substantial improvement of proportioning systems in the field of biotechnology might result, inter alia, in progress in breeding useful plants and useful animals and in controlling infectious diseases provoked by fungi, bacteria and viruses.

EP 0 725 267 A2 discloses a microproportioning system which has a micro-injection pump and a micro-diaphragm pump. To fill the system, the exit of the micro injection pump configured as a pipette tip may be dipped into a reservoir for the liquid being proportioned. The liquid is then delivered into the system by means of the micro-diaphragm pump, the entrance of which is connected to the micro-injection pump.

To clean the system, the exit of the micro-injection pump may be dipped into a stock for scouring liquid. The scouring liquid will also be delivered from the micro-diaphragm pump, the entrance of which is connected to the micro-injection pump, to a waste tank.

DE-A-41 40 533 relates to a microproportioning apparatus for the expulsion of minimal lubricant doses in the form of strands or droplets. A supply conduit for feeding the lubricant may open into the chamber of the apparatus at the side or the backward end of a tubular duct. The lubricating oil is drawn in via the supply conduit by deforming a bilaminar lamella. When an electric voltage is applied to a transducer the bilaminar lamella will bulge inwards and displace the lubricating oil so that the dose is expelled as droplets or a short strand through an outlet nozzle.

With this in view, it is the object of the invention to create a precise and simple microproportioning system having a proportioning volume in the range of a few nanoliters to a few microliters.

SUMMARY OF THE INVENTION

This and other objects of the present invention, which will become apparent hereinafter are achieved by providing a microportioning system including, according to the first embodiment:

a reservoir,
    a micro-diaphragm pump the entrance of which is connected to the reservoir,
    an open-jet proportioner the entrance of which is connected to the exit of the micro-diaphragm pump,
    a proportioning port connected to the exit of the open-jet proportioner, and a proportioning control which is in an operative communication with the micro-diaphragm pump and the open jet proportioner.

The reservoir may be precharged with liquid with the aid of external means or may be tilled with liquid by means of the micro-diaphragm pump prior to or after its integration in the microproportioning system. The liquid may be a reagent, e.g. an enzyme. The micro-diaphragm pump may further pump liquid to the open jet proportioner from the reservoir or from outside. The open jet proportioner may dispense the liquid, which was pumped in, in an open jet. The capability of pumping in an open jet makes possible the no-entrainment proportioning of volumes being proportioned in the range from a few nanoliters to a few microliters at high proportioning accuracies. When the micro-diaphragm pump operates and the open-jet proportioner is at rest the system may allow a liquid volume to flow off from the proportioning port, which can be proportioned onto a substrate. Even major volumes being proportioned may be dispensed here. Further, the micro-diaphragm pump is adapted, with the open-jet proportioner at rest, to drive an auxiliary liquid column (e.g. water) which may originate from the reservoir or may be drawn in from outside, the auxiliary liquid column functioning as a pipette piston of an air cushion or tight-state displacement system.

The volume being proportioned may be controlled, when dispensed in an open jet, via the displacement volume of the open-jet means and, for the rest, via the stroke volume or several stroke volumes of the micro-diaphragm pump.

According to a second embodiment of the present invention, a microproportioning system includes:

a compressible reservoir from which liquid is adapted to be filled by compression into an open-jet proportioner the entrance of which is connected to the reservoir, a proportioning port connected to the exit of the open-jet proportioner, and a proportioning control means which is in an operative communication with the micro-open jet proportioner.

The reservoir may be filled with liquid (e.g. a reagent, an enzyme) with the aid of eternal means prior to or after its integration in the microproportioning system. The open-jet proportioner is filled through a single or multiple compression of the reservoir. To this end, the reservoir may have a movable wall which is accessible iron outside. After the filling process, delivery of liquid in an open jet may be effected from the proportioning port. Fur this purpose, the proportioning control will control the open jet proportioner into the open jet mode. The volume being proportioned may be controlled via the displacement volume of the open jet proportioner.

According to a third embodiment of the present invention, a microproportioning system includes a single reservoir an open-jet proportioner the pressure chamber of which is the aforementioned reservoir, which is opened towards a proportioning port, and a proportioning control means which is in an operative communication with the open-jet proportioner.

The pressure chamber of the open jet proportioner may be filled with liquid with the aid of external means prior to or after its integration in the system. For delivery of the liquid from the proportioning port in an open jet, the proportioning control will control the open-jet means into the open-jet mode. The volume being proportioned may be controlled via the displacement volume of the open jet proportioner, i.e. via the volume displaced by means of the motion of the diaphragm of the open-jet proportioner. For the delivery of several volumes being proportioned, the displacement volume of the diaphragm may be controlled by several steps.

According to a fourth embodiment of the present invention a microproportioning system includes:

a reservoir, a micro-diaphragm pump the entrance of which is connected to the reservoir, a proportioning port connected to the exit of the micro-diaphragm pump, and a proportioning control means which is in an operative communication with the micro-diaphragm pump, wherein the micro-diaphragm pump and the reservoir are combined to form one constructional element exchangeably connected to an actuator module in a microsystem technology or hybrid technology.

The reservoir may be filled with liquid (e.g. a reagent, an enzyme) from outside prior to or after its integration in the system or may be filled by means of the micro-diaphragm pump, which can be appropriately controlled by the proportioning control. For delivery of liquid from the proportioning port, the proportioning control will control the micro-diaphragm pump into the pumping mode. The volume being proportioned may be controlled via the stroke volume of the micro-diaphragm pump. After the system is emptied the micro-diaphragm pump and the reservoir, which are combined to form an exchangeable constructional element in a microsystem technology or hybrid technology, may be exchanged against another constructional element which can already be precharged.

The actuator module especially has the function of a holder for the constructional element and can especially be a handle (for a hand-portable unit) or a stationary device. As a general principle, the actuator module may have all components of the system which do not form part of the exchangeable constructional element. A connection or coupling of such components to the element may particularly be effected mechanically, via electric plug-and-socket connectors, optocouplers etc. The actuator module may particularly comprise actuating means (switches, push-button switches, mounting elements etc.) and/or signalling means (LCD display etc.) and/or driving means and/or the proportioning control. This also applies to all of the other embodiments which may have an actuator module.

According to a fifth embodiment of the present invention, a microproportioning system including a reservoir, a micro-diaphragm pump the entrance of which is connected to the reservoir, a proportioning port connected to the exit of the micro-diaphragm pump, and a proportioning control means which is in an operative communication with the micro-diaphragm pump and controls the displacement of an auxiliary liquid column from the reservoir for the suction of liquid through the proportioning port or an expulsion of liquid from the proportioning port by controlling the micro-diaphragm pump into the pumping mode in the one or the other direction.

The reservoir may be filled with auxiliary liquid prior to or after its integration in the system. Also for this variant, the auxiliary liquid forms a piston which—like a pipette piston—draws in or expels liquid through the proportioning port. The volume being proportioned can be controlled via the stroke volume of the micro-diaphragm pump which is known or can be determined on the basis of a calibration along a measuring length. Also, the volume being proportioned may be controlled by displacing the auxiliary liquid column along a given length, which corresponds to the proportioned volume desired.

According to a sixth embodiment of the present invention, a microproportioning system includes a reservoir having a capillary balance system, an open jet proportioner the entrance of which is connected to the capillary balance system, a proportioning port connected to the exit of the open-jet proportioner, and a proportioning control means which is in an operative communication with the open-jet proportioner.

The capillary balance system serves for the storage and capillary transport of the liquid from the reservoir to the open-jet proportioner. In addition to this, it may serve for balancing out variations of environmental conditions such as air pressure and temperature and of the liquid volume consumed by the open jet proportioner. The capillary balance system comprises one or more capillaries joined to each other which constitute the storage volume of the reservoir. It may have at least one capillary of a meander-shaped or preferably spiralled configuration.

It is exclusively because of the action of capillary forces that the capillary balance system is adapted to transport liquid from the reservoir to the open jet proportioner to the entrance of which it is connected. This generally does not require any additional suction or pressure forces that would have to be applied, for example by means of an extra pump or a compressible reservoir.

To dispense the liquid from the proportioning port in an open jet, the proportioning port controls the open-jet proportioner into the open-jet mode. At this point, the capillary forces may cause uniform liquid transport to the open-jet proportioner. Moreover, when an open jet is dispensed the capillary balance system is adapted to prevent liquid from being forced back to the reservoir.

The capillary balance system prevents bubbles which are apt to interfere with the proportioning process from occurring in the liquid volume stored when there is an acceleration such as a fall of the reservoir. This is the case especially for meander-shaped and spiralled runs of the capillary because forces perpendicular to the wall of the capillary will substantially occur in case of an acceleration. Moreover, a no-corner or little-corner and no-edge or little-edge run of the capillary as is especially possible in meander-shaped or spiralled runs of the capillary will favour the filling of the reservoir with no inclusion of bubbles.

The capillary balance system may be aerated at least at one point remote from the connection to the open jet proportioner in order that a flow-out of liquid be compensated by air flowing behind. The capillary forces will simultaneously prevent any flow-out from the reservoir. The capillary balance system, however, may also be closed by a slug migrating along with the liquid, which prevents the liquid from contacting the environment and, additionally, counteracts a flow-out. It is understood that the reservoir with the capillary balance system may also be designed as a compressible one.

A reservoir having a capillary balance system can also be used advantageously in the remaining embodiments of a microproportioning system.

According to a seventh embodiment of the present invention a microproportioning system including
- a reservoir in plastic,
- a substantially panel-shaped delivering means designed as a constructional element in a microsystem technology including a micro-diaphragm pump and/or an open jet proportioner wherein the reservoir and the constructional element are fixed to each other in an overlaying relationship and the entrance of the conveying device is connected to the reservoir,
- a proportioning port connected to the exit of the delivering means, and
- a proportioning control means which is in an operative communication with the delivering means.

Thus, such microproportioning system is based on a hybrid constructional element, which comprises the reservoir in plastic and the delivering means in a microsystem technology. This will favour relatively large-volume reservoirs unlike those for a microproportioning system in which the reservoir and the delivering means are designed as a constructional element in a microsystem technology. At the same time, this aspect will favour the structure of the microproportioning system, especially when the hybrid constructional element is exchangeably connected to an actuator module.

An appropriate hybrid constructional element may advantageously exist also in the remaining embodiments of a microproportioning system.

According to an eighth embodiment of the present invention a microproportioning system includes:
- a reservoir,
- a delivering means including a micro-diaphragm pump and/or an open jet proportioner the entrance of which is connected to the reservoir,
- a proportioning port connected to the exit of the delivering means,
- a proportioning control means which is in an operative communication with the delivering means,
- an actuator module to which the constructional element comprising the reservoir is exchangeably connected, and
- a temperable carrier into which the constructional element removed from the actuator module is adapted to be inserted.

This microproportioning system will favour the proportioning of temperature-sensitive substances. The constructional element comprising the reservoir may comprise at least a further component of the microproportioning system, for example at least some part of the delivering means and/or the proportioning control. It may be designed as a hybrid constructional element or in a microsystem technology as a whole. Inserting the constructional element into a temperable carrier prior to and/or after the proportioning process will permit to temper the liquid being proportioned in a well-defined and, hence, energetically favourable way. The carrier may serve for storing one or more constructional elements in a laboratory refrigerator. However, it may also serve for transporting at least one constructional element between a refrigerator and the workplace. The carrier is further adapted to temper the constructional elements at the workplace. It will particularly be passive tempering systems which are taken into consideration for the carrier, for example those having a cooling accumulator filled with a brine. It may also have an active tempering system, however, especially one including a Peltier element. The system is particularly suited for proportioning enzymes.

As far as the remaining embodiments of a microproportioning system have an exchangeable constructional element comprising the reservoir they may also have a temperable carrier.

According to the ninth embodiment of the present invention, a microproportioning system includes:
- a reservoir,
- a delivering means including a micro- diaphragm pump and/or an open jet proportioner the entrance of which is connected to the reservoir,
- a proportioning port connected to the exit of the delivering means,
- a proportioning control means which is in an operative communication with the delivering means,
- wherein a constructional element comprising the reservoir and/or the delivering means is exchangeably connected to an actuator module and has a coding and the actuator module has a sensing device for coding the constructional element.

The coding may relate to an information on a filling substance and/or one or more proportioning characteristics of the exchangeable constructional element. It may contain an information on which enzyme is in a reservoir, on when the reservoir was filled, on an expiry date, on which volume or residual volume of liquid is contained in the reservoir, on which volume being proportioned the delivering means dispenses in case of a certain actuation or activation, etc. The actuator module can sense the coding by means of the sensing means so that the information may be displayed or otherwise exploited after undergoing processing by an evaluating means if need be.

Accordingly, the remaining embodiments of a microproportioning system may also be equipped with a coding and a sensing means as far as they have a constructional element which is exchangeably connected to an actuator module.

According to a tenth embodiment of the present invention a microproportioning system includes:

a reservoir, a delivering means including an open-jet proportioner or, if need be, a micro-diaphragm pump the entrance of the delivering means being connected to the reservoir, a proportioning port connected to the exit of the delivering means, a proportioning control means which is in an operative communication with the delivering means, and a light source for a light beam the emission axis of which is aligned with respect to the proportioning port such that the light beam marks the axis of motion and/or the point of impingement of the liquid dispensed from the proportioning port.

In an open-jet dispensing mode, the microproportioning system may expel drops or fluid beams the whole liquid volume of which is typically in the range of 10 to 200 nl. These may not be discerned with the naked eye, which will impair precise-target proportioning. The light source designates the path of motion and/or the point of impingement of the liquid, thus enabling the volume being proportioned to be safely fed to the desired place. This "light-beam pointer" is preferably employed in designs where the microproportioning system is a portable unit. It may be integrated in the microproportioning system by means of a laser diode. Alignment of the light beam may be effected directly, via an optical guide or via an integrated optical-guide structure of a constructional element of the microproportioning system in a microsystem technology.

Such a light-beam pointer may advantageously also exist in the remaining embodiments of a microproportioning system, which include an open-jet proportioner.

Some terms of this application will now be explained in detail:

A "microproportioning system" is a proportioning system which comprises at least one component in a microsystem technology.

A "component in a microsystem technology" is a preferably micromechanical component which is manufactured at least partially in a semiconductor technology, preferably a silicon technology.

The micro-diaphragm pump the open-jet proportioner and/or other constructional elements of the inventive microproportioning systems may be compactly manufactured in a microsystem technology from a semiconductor chip or several semiconductor chips in a hybrid construction. Also, components in a microsystem technology may be combined with conventional components, e.g. a reservoir in plastic, to form a hybrid constructional element.

A "micro-diaphragm pump" is a diaphragm-type pump in a microsystem technology with a pumping chamber including an inlet and an outlet, a pump diaphragm associated therewith, and an electrostatic, piezoelectric, thermomechanical or like-type drive or actor associated therewith.

What is characteristic of a micro-diaphragm pump is that it pumps the liquid against a counterpressure restricted with regard to overcoming capillary forces, viscosity forces, and surface tensions. The pumping pressure is insufficient to expel the liquid from the proportioning port, i.e. dispense it in an open jet. Rather, the liquid runs or drops out of the proportioning port because it is driven by gravitational acceleration. However, a micro-diaphragm pump—when compared to an open-jet proportioner—may typically pump large volumetric flow rates. It is particularly suited for continuous operation and is adapted to effect pumping in different directions depending on its construction. What further is typical—but not conclusively necessary—is the presence of active or passive valves at the inlet and/or outlet of the pumping chamber.

An "open-jet proportioner" is a proportioning member having a pressure chamber on which a pressure pulse may be applied to any liquid contained by means of a diaphragm and an actor acting thereon, which will cause the expulsion of liquid from a proportioning port. Typically—but not necessarily—, the proportioning port of the open-jet proportioner is formed on a nozzle. Hence, an open jet proportioner will be capable of accelerating a liquid volume in such a way that the liquid/solid interfacial tension is overcome at the proportioning port and the liquid volume is catapulted out. Depending on the volume accelerated, a drop or beam formation will occur. The open-jet proportioner is preferably an element in a microsystem technology, but need not necessarily be designed according to a microsystem technology.

BRIEF DESCRIPTION OF THE DRAWINGS

The invention will now be described in detail with reference to the accompanying drawing of some embodiments. In the drawings:

FIGS. 19 and 20 show a perspective view of a fluid module in an actuating module having a light-beam pointer above a substrate (FIG. 19) and a side view of a fluid beam and a light beam of the same modules;

FIG. 21 shows a perspective view of a proportioning chip having an integrated light-conducting structure.

DETAILED DESCRIPTION OF THE PREFERRED EMBODIMENTS

Identical components are designated by the same reference numbers in the various embodiments.

Figure 1:
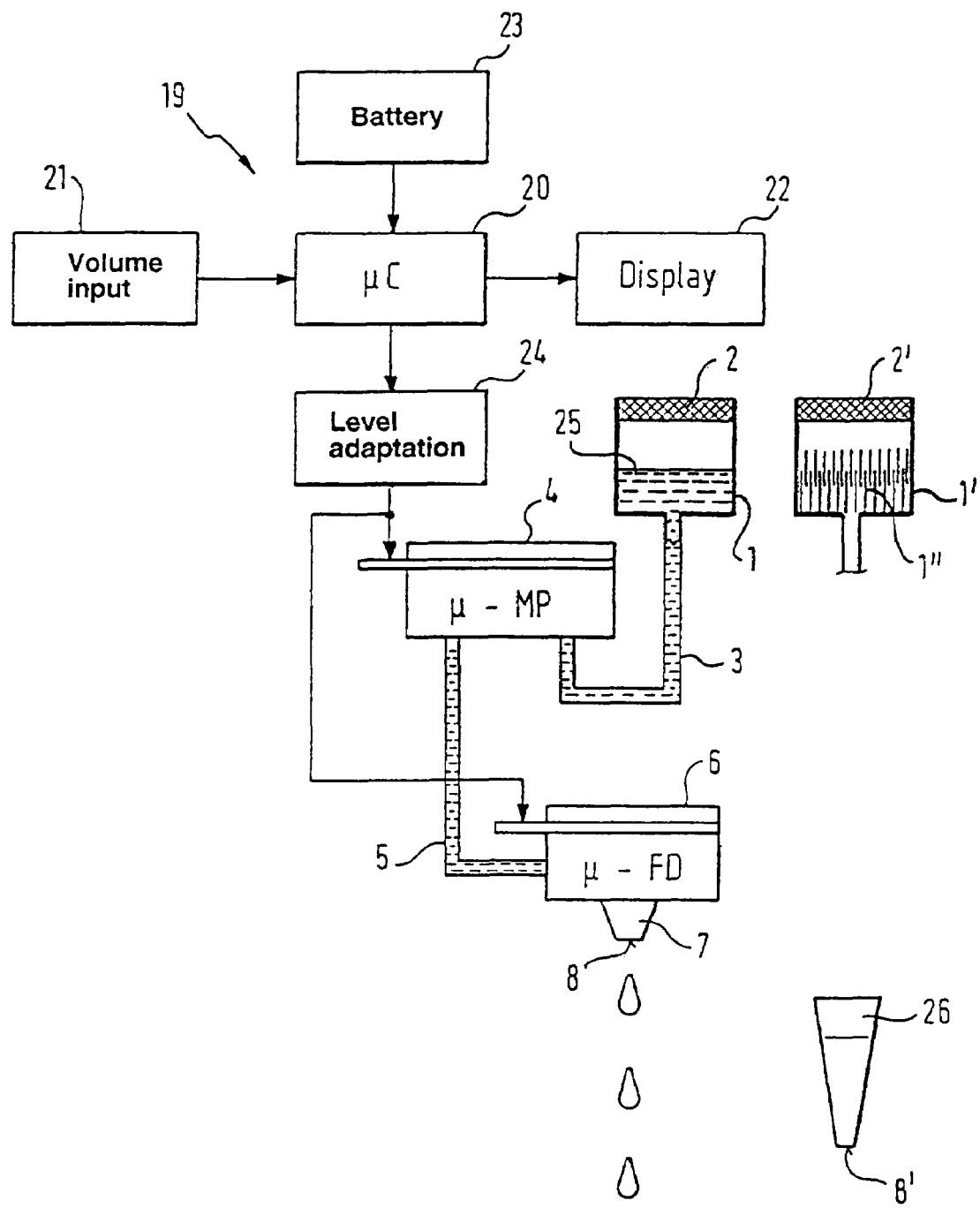
FIG. 1 shows a schematic block diagram of a combined microproportioning system for proportioning in an open jet onto a substrate or for pipetting.

The microproportioning system of FIG. 1 has a reservoir 1 which includes a filter 2 at top for pressure balance with the environment and is connected at bottom to the entrance of a micro-diaphragm pump 4 via a line 3. The exit thereof is joined, via a line 5, to the entrance of an open-jet proportioner 6 which has a nozzle 7 with a proportioning port 8 at its exit end.

Figure 2:
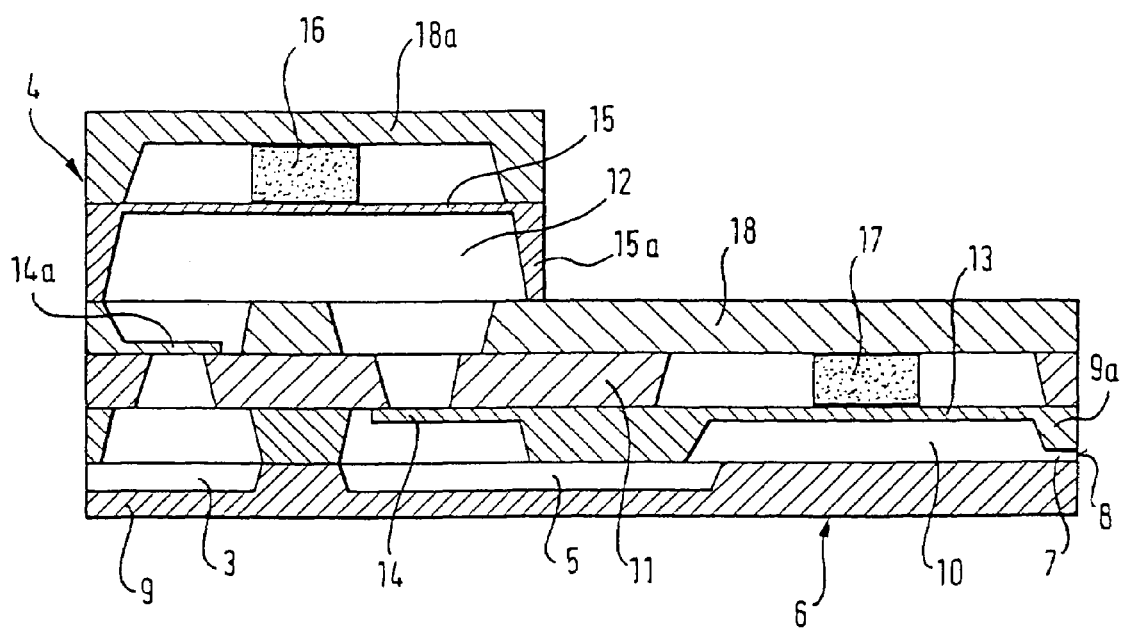
FIG. 2 shows a schematic longitudinal section of the microsystem technical structure of the micro-diaphragm pump and the open-jet proportioner of the same system.

FIG. 2 shows an example of the microsystem technology design of micro-diaphragm pump 4 and open-jet proportioner 6 in a single component. Such components are composed of several semiconductor layers. Lines 3 and 5 are formed in the lowermost layer 9. Housed in the overlying layer 9a is pressure chamber 10 of open-jet proportioner 6 and the outlet valve 14 of micro-diaphragm pump 4. It further has a diaphragm 13 associated with pressure chamber 10. Layer 11 disposed over it has included therein the end portions of lines 3 and 5. A fourth layer 18 constitutes inlet valve 14a of micro-diaphragm pump 4 and the countersupport of the piezoelectric actuator 17 for diaphragm 13. The layer 15a disposed over it constitutes pumping chamber 12 of micro-diaphragm pump 4 with the associated diaphragm 15. Diaphragm 15 is acted on by an actuator 16, which is sustained on layer 15a by means of a bridge-shaped countersupport 18a.

When diaphragm 15 of micro-diaphragm pump 4 bulges out upwardly the pump draws in liquid through line 3 in the non-return valve 14a. Subsequently, diaphragm 15 is moved back to the initial position which is shown and liquid is pressed into line 5 and pressure chamber 10 through non return valve 14a with the liquid prevented from exiting into line 3. Subsequently, the piezoelectric actuator 17 causes an abrupt size reduction of pressure chamber 10 and the liquid is expelled through nozzle 77.

As shown in FIG. 1, there is a proportioning control means 19 which has a micro-controller 20, an operating panel 21 (including a volume input), a display 22, and a power supply in the form of a battery 23. Microcontroller 20 is connected to micro-diaphragm pump 4 and open-jet proportioner 6 via a level adapter 24. The system may be operated by the proportioning control means 19 as follows:

When reservoir 1 has already been precharged with liquid 25 open jet proportioner 6 may be filled with liquid by means of diaphragm-type pump 4. The liquid filled in will then be expelled out of nozzle 7 by open jet proportioner 6 in an open jet. The volume being proportioned is determined by the activation unit of the open-jet proportioner, which especially has an effect on its positive displacement volume. However, the system may also be filled by causing diaphragm-type pump 4 to run in an inverse sense, drawing in liquid through nozzle 7 of open jet proportioner 6 and pumping it into reservoir 1.

Moreover, liquid 25 may be pumped by diaphragm-type pump 4 out of reservoir 1 through the non-operative open-jet proportioner 6 so that it flows off through nozzle 7. This way of proportioning enables proportioning to be effected on a substrate in case of a major volumetric flow rate. The volume being proportioned may be controlled via the known stroke volume of diaphragm-type pump 4.

In another mode of operation, a column of an auxiliary liquid 25 is driven by diaphragm-type pump 4. The column acts as an inert-action pipette piston which draws in or expels external liquid through nozzle 7. An exchangeable pipette tip 26 having a proportioning port 8' may be slid onto nozzle 7 for liquid reception. To minimize the air cushion between the liquid column and the liquid being proportioned, the liquid column may be forced in up to pipette tip 26. After the proportioning process, some part of auxiliary liquid 25 may be discarded by pumping it out of nozzle 7.

In lieu of reservoir 1, a reservoir 1' having a filter 2' and a capillary balance system 1" may be used, which uniformly refeeds liquid and prevents it from flowing out.

Figure 3:
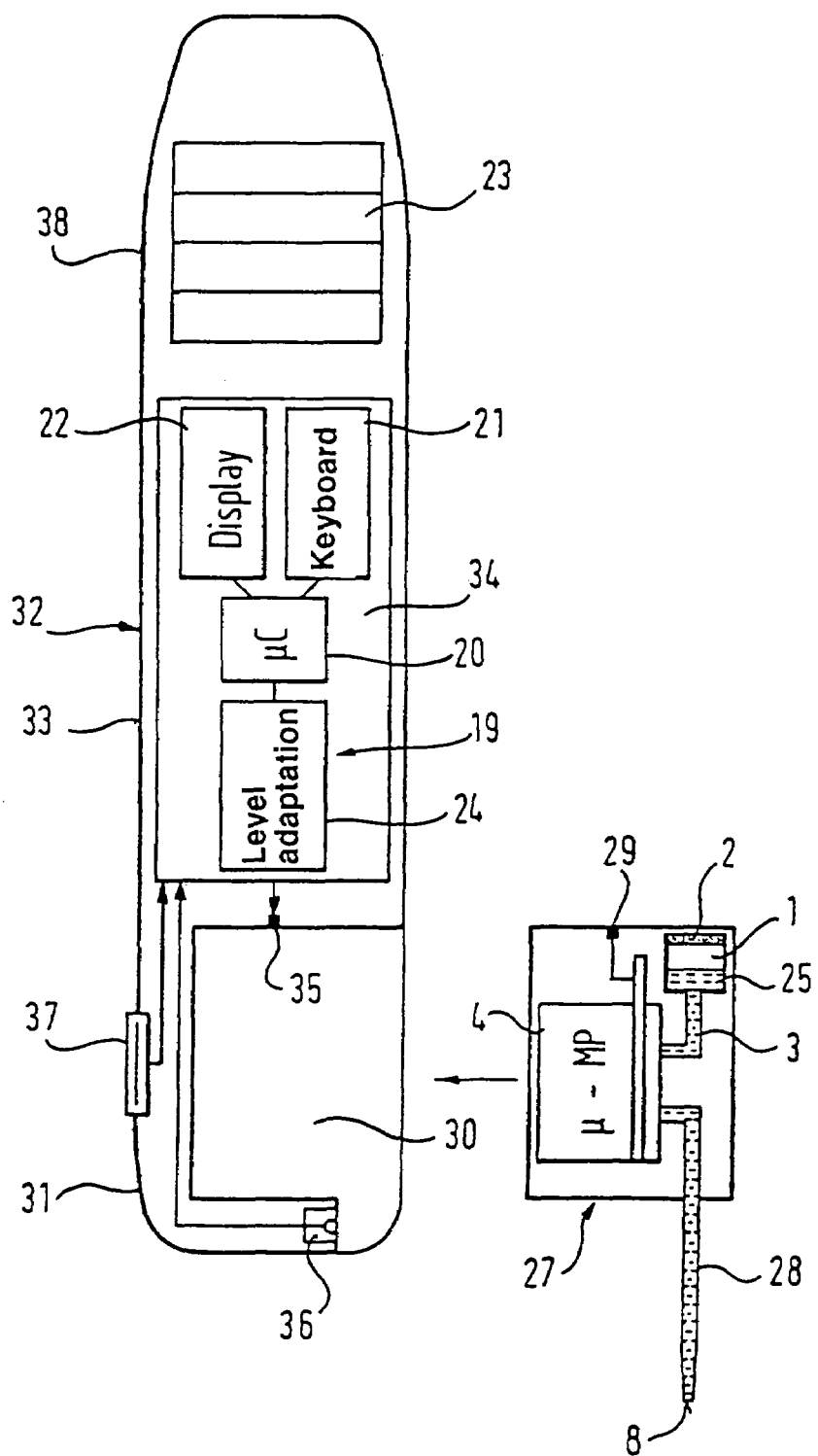
FIG. 3 shows a schematic block diagram of a dispenser having an exchangeable proportioning and reagent unit.

The microproportioning system of FIG. 3 has a proportioning and reagent unit 27 in a microsystem technology. This has a reservoir 1 with a filter 2 for pressure balance with the environment and a micro-diaphragm pump 4 connected thereto via a line 3. In lieu thereof or in addition thereto, it may have an open jet proportioner. It further has an outwardly projecting dispensing tube 28 with a proportioning port 8. Finally, an electric contact 29 is provided to couple micro-diaphragm pump 4 to a proportioning control means 19.

The proportioning and reagent unit 27 may be laterally inserted in a seat 30 in the base area 31 of a shell 32 so that dispensing tube 28 axially protrudes beyond the base area. Disposed in the central region 33 of shell 32 on a printed circuit board 34 is proportioning control means 19, which possesses microcontroller 20, operating panel 21 display 22, and level adapter 24. The proportioning control means 19 is connected, in seat 30, to a counter-contact 35 which interacts with contact 29 of proportioning and reagent unit 27. Proportioning control means 19 is further connected to an optical sensor 36 which is firmly disposed in the shell base 31 and is associated with dispensing tube 27 of the insertable proportioning and reagent unit 27. The proportioning control 19 is then connected to a dispenser key 37 which is located at the side of shell base 31. Finally, it has a connection to a battery 23 in the head region 38 of shell 1.

This proportioning system is prepared for operation by inserting a proportioning and reagent unit 27 precharged with a reagent (e.g. an enzyme) in seat 30. The mode of operation and the volume being proportioned may be preset via keyboard 21. In the first proportioning step, micro-diaphragm pump 4 pumps liquid 25 from reservoir 1 until sensor 36 detects the meniscus and, thus, reaches a defined zero position. Subsequently, the volume being proportioned will be controlled via the known stroke volume of micro-diaphragm pump 4. For more proportioning processes, proportioning control means 19 may proceed on the fact that the liquid column is in place for use at the end of dispensing tube 28. Minor reagent volumes may be discarded between the proportioning processes to avoid entrainments. Once proportioning and reagent unit 27 is emptied it is replaced with a new, precharged unit. Instead, however, it may be topped up through dispensing tube 28 when micro-diaphragm pump 4 is operated in an inverse direction.

Figure 4:
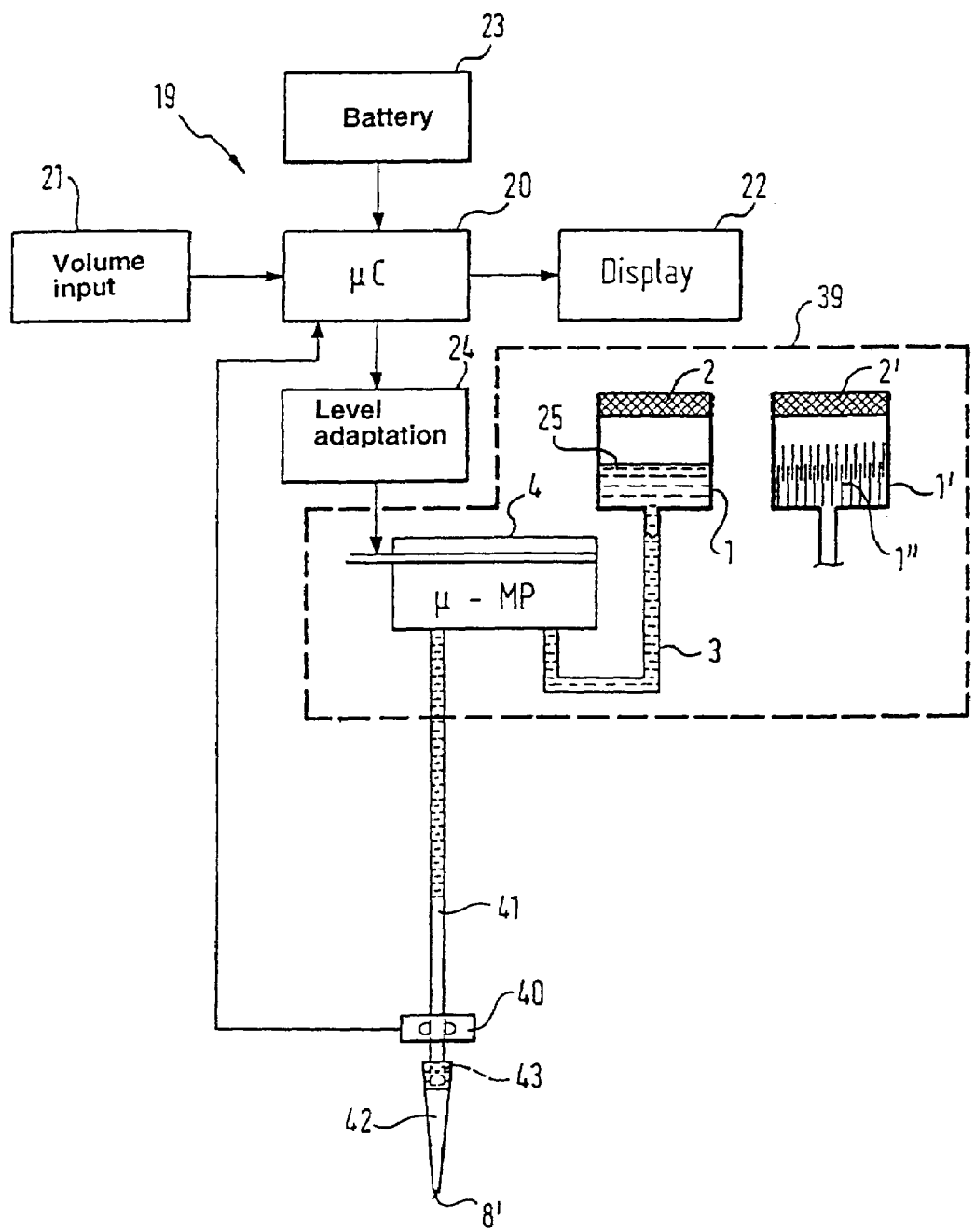
FIG. 4 shows a schematic block diagram of a pipette having an inert-action piston.

The microproportioning system of FIG. 4 has a reservoir 1 using pressure balance with the environment via a filter 2, which is connected to a micro-diaphragm pump via a line 3. Reservoir I and micro-diaphragm pump 4 are combined to form an exchangeable pumping unit 39 with the reservoir being precharged with an auxiliary liquid 25. Further, there is a proportioning control means 19 including the microcontroller 20, operating panel 21, display 22, and power supply 23, which is connected to micro-diaphragm pump 4 via a level adapter 24 (and disconnectable contacts). Moreover, microcontroller 20 has a communication to an optical sensor 40, which is associated with a dispensing line 41 connected to the exit of micro-diaphragm pump 4. Fixed to the end of dispensing line 41 is an exchangeable pipette tip 42, which has an aerosol filter 43 at its slip-on port and a proportioning port 8' at its end.

This system operates as an air cushion pipette. To this effect, auxiliary liquid 25 is displaced by micro-diaphragm pump 4 so that the liquid column is detected by sensor 40. The system has then reached its zero position. According to the volume desired to be proportioned, micro-diaphragm pump 4 displaces the liquid column so that it draws in liquid being proportioned into pipette tip 42 and expels it therefrom in the way of a pipette piston. The volume desired to be proportioned is reached by means of the control of the known stroke volume of micro-diaphragm pump 4. After a proportioning process, pipette tip 40 and some part of the liquid column may be discarded. Once the auxiliary liquid 25 is used up a new pumping unit 39 will be inserted.

Figure 5:
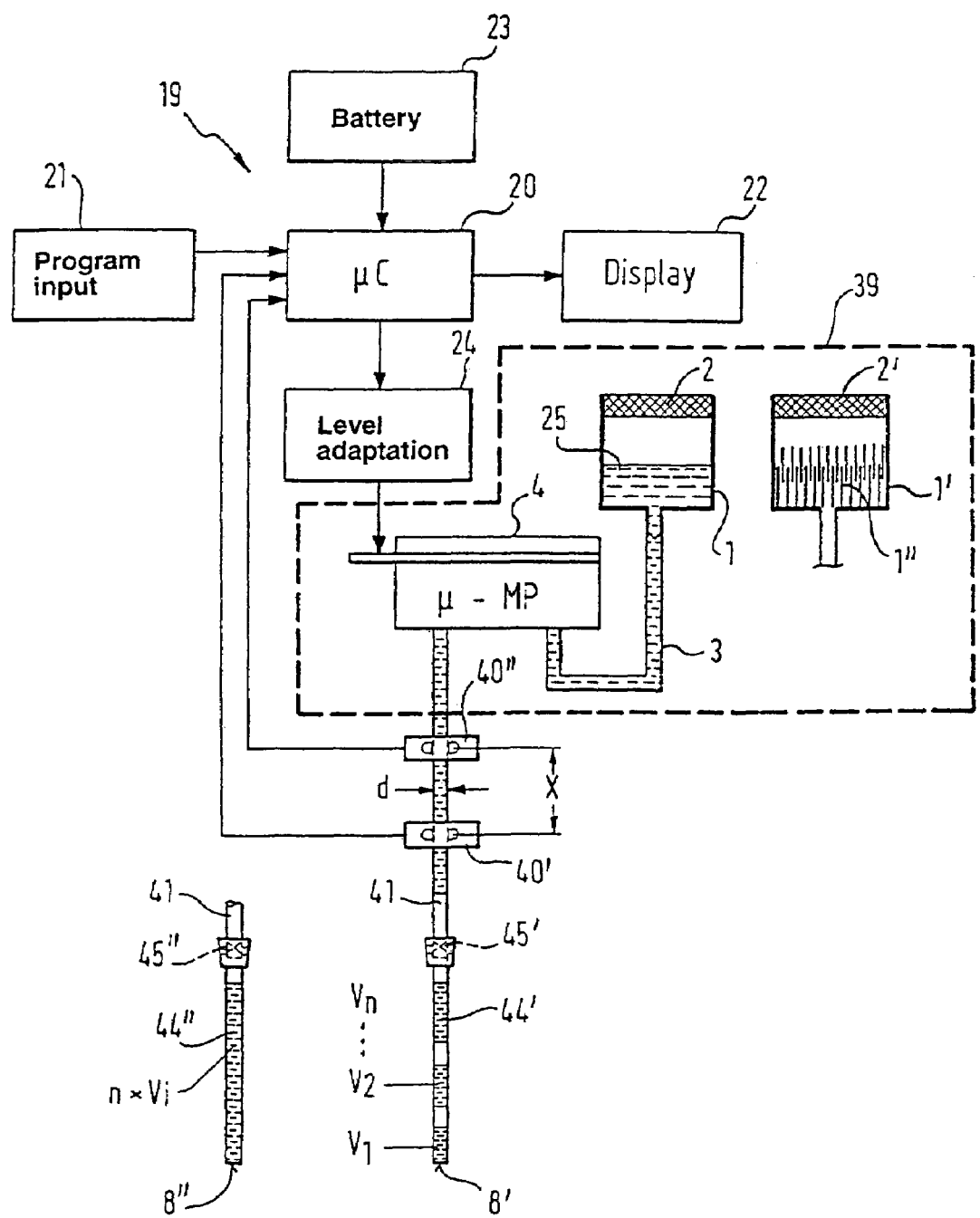
FIG. 5 shows a schematic block diagram of a dispenser/diluter having an inert-action piston and a calibration length.

The embodiment of FIG. 5 also operates according to the air cushion principle. As a distinction from the preceding embodiment, two sensors 40', 40", which are associated with dispensing line 41 of diameter d at a spacing x from each other are connected to proportioning control means 19. In addition, diluting tubes (diluters) 44' or dispensing tubes (dispensers) 44", which have an aerosol filter 45', 45" each in the communication area and proportioning ports 8'. 8" at the other end are adapted to be connected to the dispensing line 41.

In this system, the control of the volume being proportioned is also based on the stroke volume of micro-diaphragm pump 4 which is reproducible and, hence, can be calibrated. At the beginning of a proportioning process (or a proportioning series) the auxiliary liquid column is displaced between the two optical sensors 40', 40" for stroke volume calibration. If a diluter 44' is attached several liquid volumes $V_1, V_2$, to $V_n$, which are separated from each other by air bubbles may be drawn and may be mixed in the desired volume ratio while being dispensed.

When a dispensing tube 44" is attached an overall liquid volume $n \times V_i$; may be drawn in and will then be dispensed by individual steps.

Figure 6:
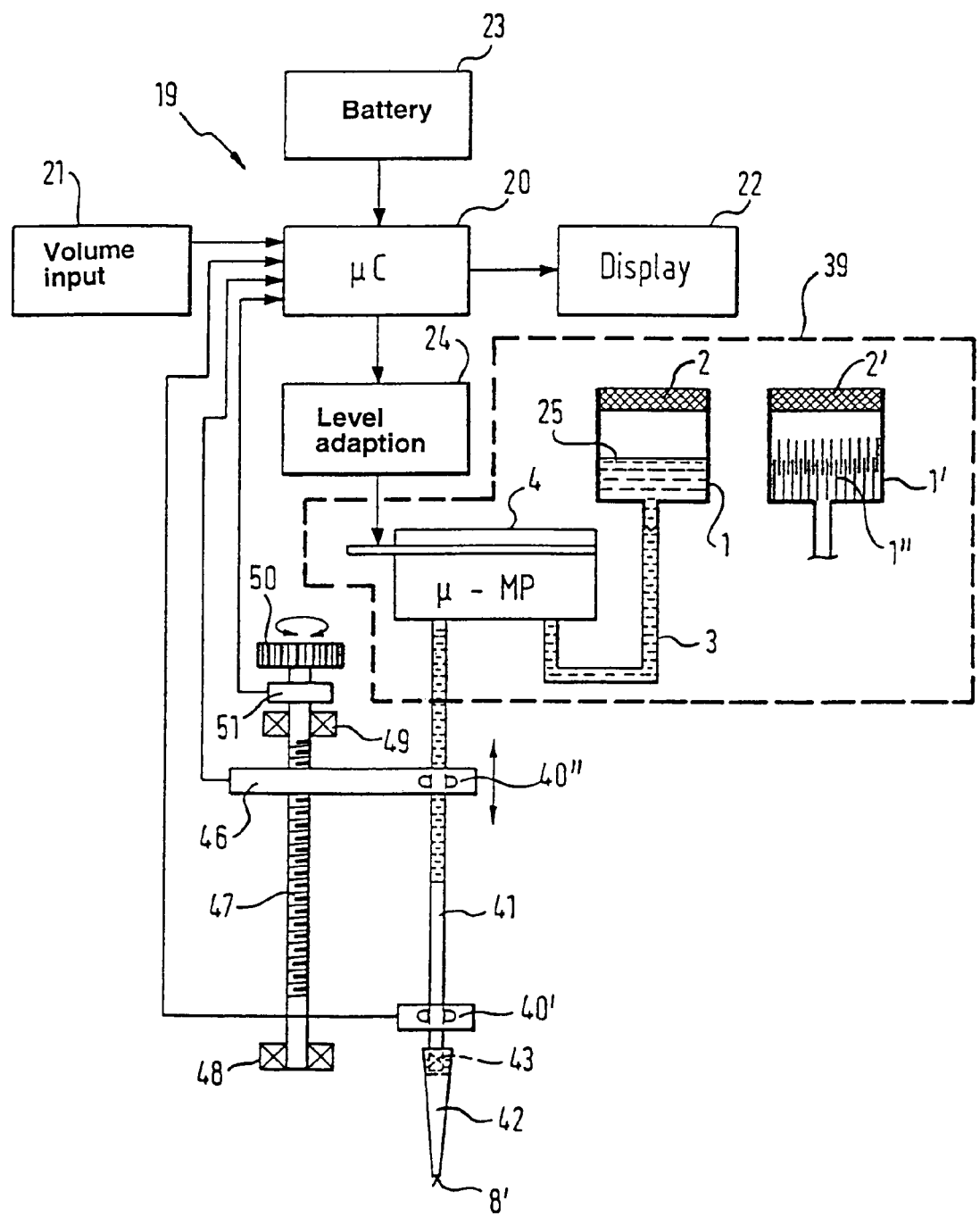
FIG. 6 shows a schematic block diagram of a pipette having an inert-action piston and an adjustable displacement length.

FIG. 6 distinguishes itself from the embodiment of FIG. 4 in that there is a second sensor 40" which is also connected to the proportioning control means 19 and is adapted to be displaced along dispensing line 41. To this effect, sensor 40" is mounted on a nut 46, which can be displaced by means of a screw 47 retained in pivot bearings 48, 49. Screw 47 has a small rotary wheel 50 for manual adjustment. Furthermore, it carries an encoder 51 which is read by the proportioning control 19.

Rotating the small wheel 50 will adjust the spacing between sensors 40', 40" in such a way that this will correspond to the volume desired to be proportioned. Proportioning control 19 will then displace the auxiliary liquid column between the positions of the sensors 40', 40" to draw liquid into pipette tip 42 and to expel it therefrom.

Figure 7:
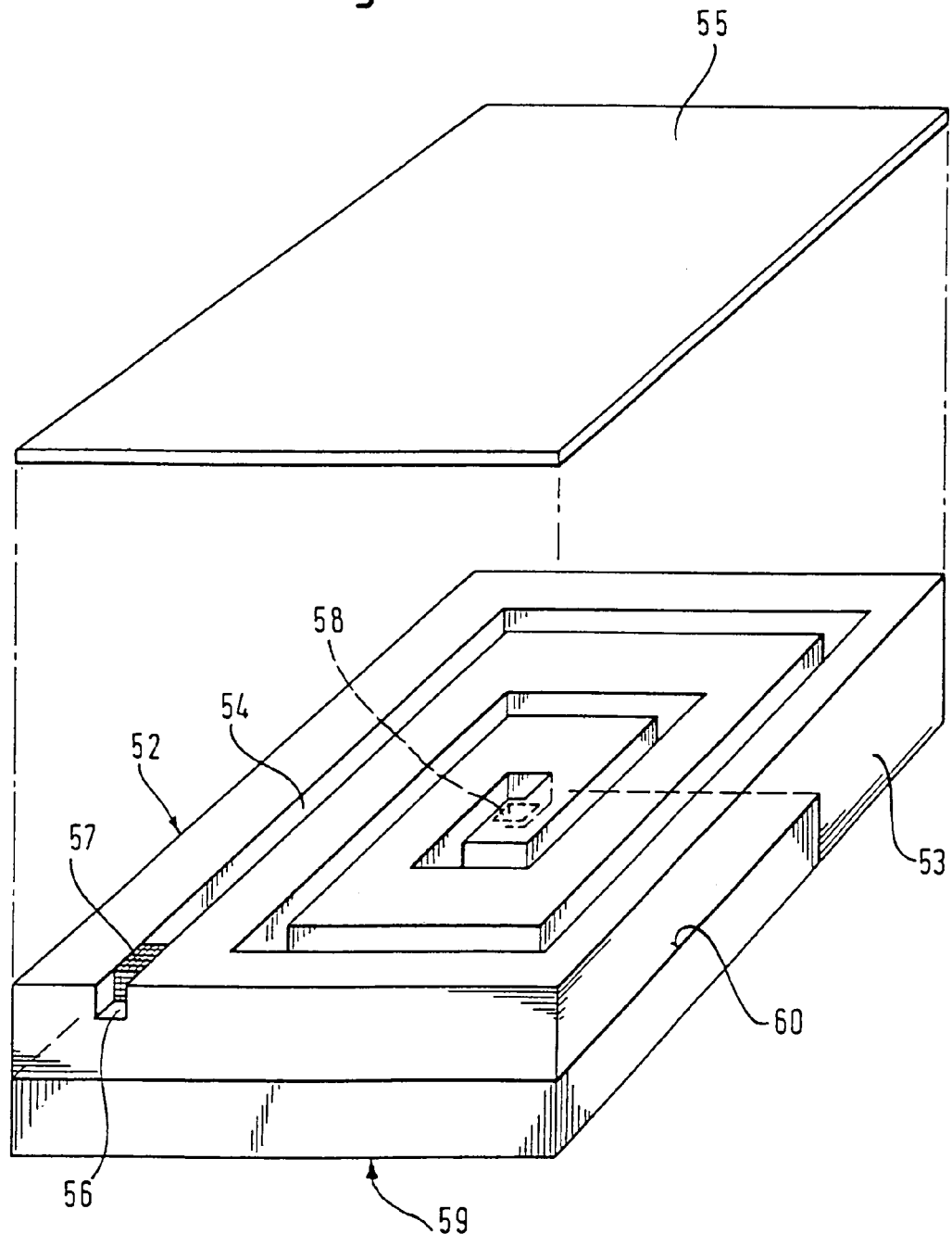
FIG. 7 shows a perspective exploded view of a reservoir having a spiralled capillary tube on a proportioning chip.

As shown in FIG. 7, a reservoir 52 has a substantially panel-shaped plastic body 53 in which a spiralled, capillary liquid duct 54 is formed which has straight and interconnected duct portions. The liquid ducts 54 is defined by a U-shaped groove which is open in an upward direction in the plastic body. At top, it is confined by a cover plate 55, which can also be in plastic. The cover plate may advantageously be welded on with no gap by a laser process, ultrasonically jointed or heat-sealed as a sheet.

The design of reservoir 52 in plastic will favour a large storage volume.

The outer end of liquid duct 54 opens into a filling port 56 in a front surface of plastic body 53. The port may be closed by means of a filter 57, which is somewhat pressed into liquid duct 54. Filter 57 enables an exchange of air while reservoir 52 is being emptied, but prevents liquid contamination by the liquid in the liquid duct and the environment. Also, wetting properties of filter 57 are adapted to prevent liquid from exiting.

A capillary passage port 58 extends across the plastic body 53 from the centre of the spiralled liquid duct 54. Passage port 58 opens above the entrance of a delivering means 59 designed in a microsystem technology. This is a panel-shaped semiconductor chip (proportioning chip), which is inserted into a step 60 at the underside of plastic body 53. Specifically, the delivering means 59 may be an open-jet proportioner.

Capillary forces acting on the liquid filled into liquid duct 54 deliver the liquid through passage opening 58 and into the conveying means 59 from which it will be dispensed. The capillary forces also counteract unintentional flow-out of liquid from the filling port 56. The spiralled arrangement of the liquid duct prevents the liquid string to break in the liquid duct 54 because of accelerations which may occur in handling, for instance as a result of a fall. The substantial consequence of such accelerations, namely, will be forces perpendicular to the wall of liquid duct 54 which prevents the occurrence of bubbles which may interfere with the proportioning process.

In lieu of filter 57, there can be a slug which will migrating along when liquid is being dispensed and does not leave residues on the wall of liquid duct 54. Specifically, it may be a highly viscous fluid slug.

A reservoir, in a way similar to a wound-paper capacitor, can have two wound-up sheets which have a small spacing from each other and define a spiralled liquid duct. Likewise, a design having a wound-up capillary (e.g. with a wound-up flexible tube) is possible, especially one having a spatial arrangement of the spiral.

Figure 8:
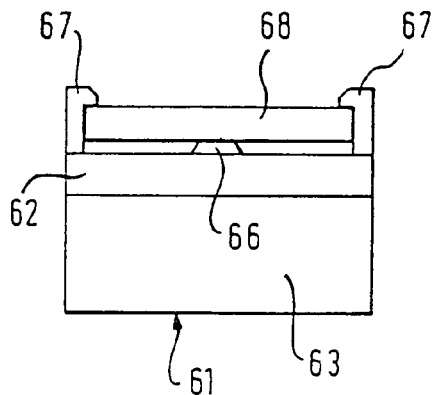
FIGS. 8 and 9 show a front view (FIG. 8) and a longitudinal section (FIG. 9) of another reservoir in a snap connection with a proportioning chip.
Figure 9:
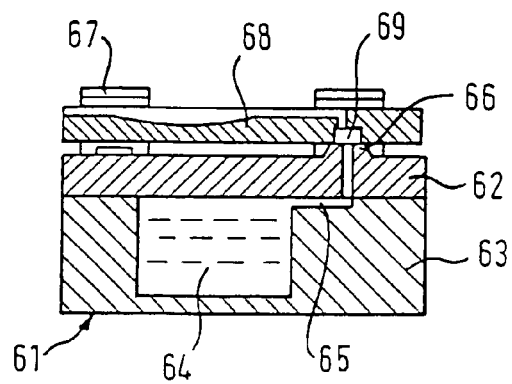

As shown in FIGS. 8 and 9, a reservoir 61 has a base plate 62 and a seating body 63 connected thereto, in which a rectangular storage space 64 is formed. Liquid is fed from storage space 64 through a feeding capillary 65 to a cone-shaped socket 66 on the other side of base plate 62.

Hooked snap elements 67 project upwards from the sides of base plate 62. By means of these snap elements 67, a delivering means having the form of a semiconductor chip (proportioning chip) 68 is held with regard to base plate 62 in such a way that socket 66 urges against a sealing surface around an entrance 69 of proportioning chip means 68. Reservoir 61 and the proportioning chip 68 together define a fluid module.

Altogether, reservoir 61 may be made of plastic material. Its formation from two parts 62, 63 favours the realization of feeding capillary 65 according to the desired shape.

Figure 10:
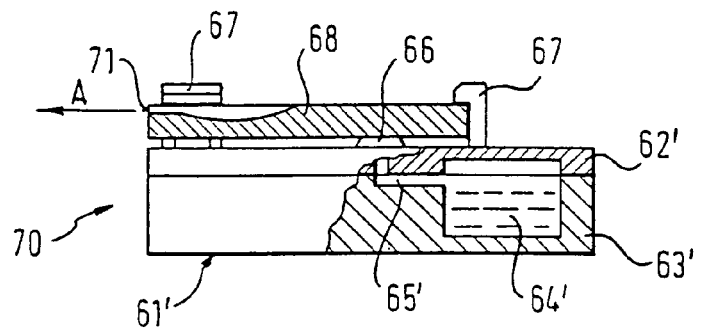
FIG. 10 shows a side view of another reservoir in a snap connection with a proportioning chip with some portions broken way.

FIG. 10 shows a similarly composed fluid module 70 in which, however, the reservoir 61' slightly projects laterally beyond the proportioning chip 68. The storage space 64' for liquid, which extends both into the base plate 62' and the accommodating body 63', is formed in the projecting portion of reservoir 61'.

The proportioning semiconductor chip 68 has its proportioning port at 71, from which liquid is dispensed in the dispensing direction (arrow A). The fluid module 70 will then be directed downwards so that the storage space 64' is always above the feeding ancillary 65'. This ensures supply to the proportioning chip 68 by gravity via socket 66 and the effect of the feeding capillary 65'.

Figure 11:
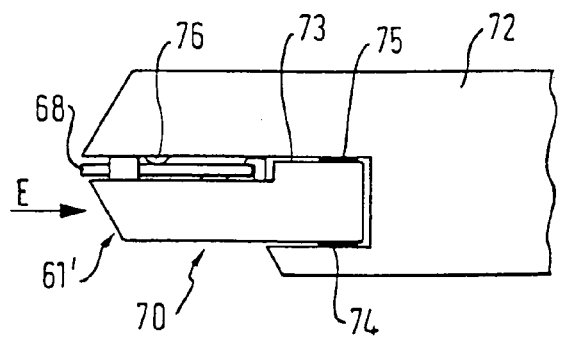
FIGS. 11 and 12 show a side view (FIG. 11) and a front view (FIG. 12) of the base region of an actuator module with a fluid module inserted according to FIG. 10.
Figure 12:
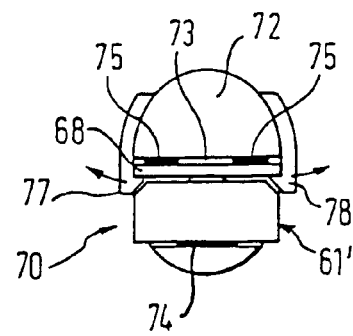

As shown in FIGS. 11 and 12, an actuator module 72 has disposed, at its lower end, an accommodation channel 73 into which a fluid module 70 shown in FIG. 10 is fitted. It is held there at the projecting portion of its reservoir 61'. In the case shown it is held between resilient contact members 74, 75 of which one urges against base plate 62' while the other one urges against the accomodating body 63'. Actuator module 72 further has associated with accomodation channel 73 an actor 76 which bears with no gap against a diaphragm of the proportioning chip 68. To this end, retaining pincers 77, 78 press the proportioning chip 68, via the diaphragm, against actor 87. The retaining pincers 77, 78 are closed at the end of the axial fitting motion of fluid module 70 into the accomodating shaft 73 in the direction E. Actuating the actor 76 may cause liquid to be expelled.

Figure 13:
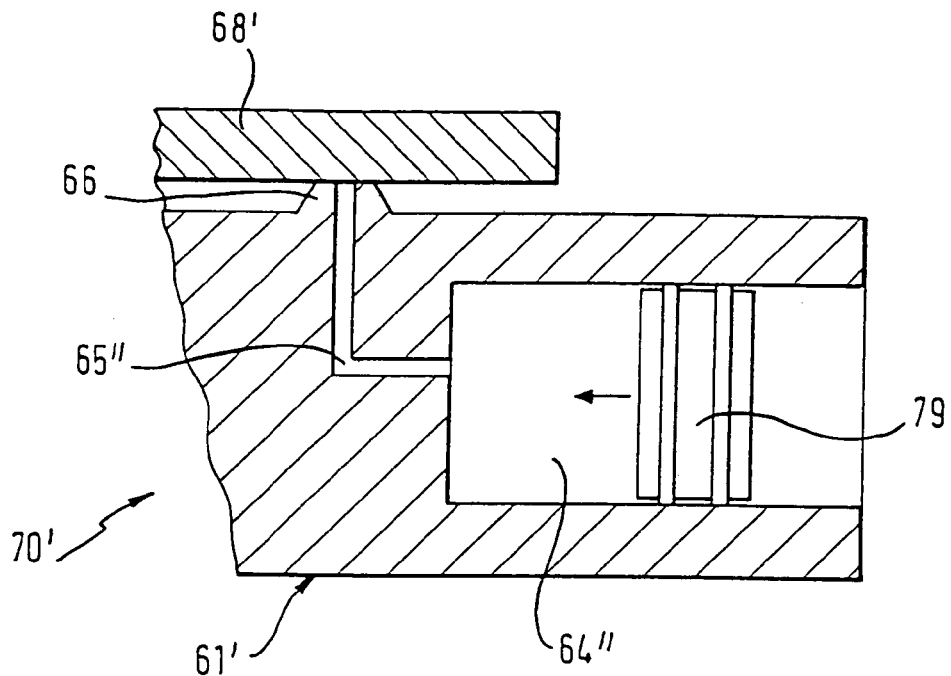
FIG. 13 shows a partial section of a reservoir having a balance piston on a proportioning chip.

FIG. 13 shows a portion of a fluid module 70' from a proportioning chip 68' and a reservoir 61' the storage space 64" of which is connected to a capillary 65" feeding the proportioning chip 68' at one end and to the atmosphere at the other end. A piston 79 is sealingly inserted into storage space 64". It closes the storage space 64" against the atmosphere and causes a pressure balance by moving up while liquid is being withdrawn through feeding capillary 65". Piston 79 may also be used, by actuating it from outside, for pressing liquid into the feeding capillary 65" and the proportioning chip 68'. Besides, piston 79 may be pulled out to refill reservoir 61'.

In lieu of a piston, there may be a highly viscous fluid slug, which migrates along encountering nearly no resistance while liquid is being withdrawn.

Figure 14:
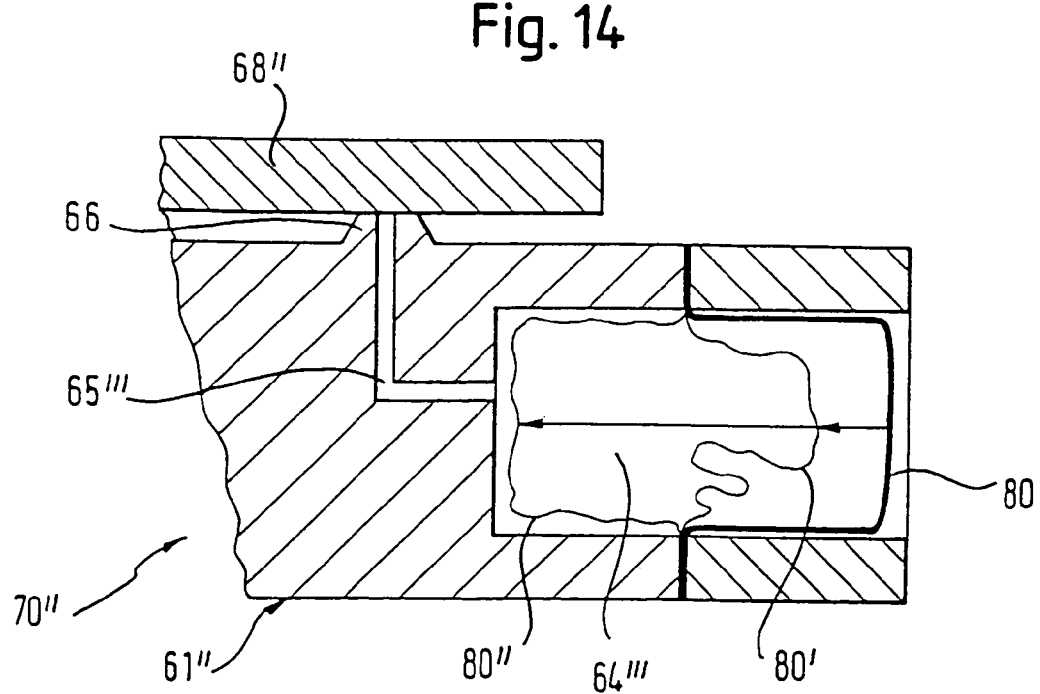
FIG. 14 shows a partial section of a reservoir having a balance pouch on a proportioning chip.

FIG. 14 shows a portion of another fluid module 70" the reservoir 61" of which also has a storage space 64'" the opening of which to the atmosphere is closed by a pouch or balloon 80 of flexible material (e.g. silicone). The reservoir 61" is divided transversely to storage space 64'" and balloon 80 is marginally clamped in the division plane between the two moulded-part halves of reservoir 61".

The balloon 80 also shields the liquid in storage space 64'" from the atmosphere. However, when liquid is delivered from storage space 64'" to the proportioning chip 68' through feeding capillary 65'" the flexible balloon 80 will adapt itself by deformation to the respective liquid volume as is suggested for two situations in weak lines 80', 80" in the drawing. Refilling is facilitated when the recovering power of the balloon 80 is negligible. A balloon 80 of resilient material is apt to support the supply of liquid to proportioning chip 68'.

The filling of storage space 64'" may be effected via feeding capillary 65'" or an additional junction. However, the balloon 80 may also consist of a material which can be pierced by the hollow needle of a charging device and will cure by itself at the point of puncture after the hollow needle is pulled out.

The fluid modules 70'" shown in FIGS. 15-19 may be of a basic structure as is particularly shown in FIGS. 7 through 10. All of them have a reservoir. However, they have a substantially box-shaped shell 81 including a dispensing head 82 at bottom which has a proportioning port at its lower end.

Figure 15:
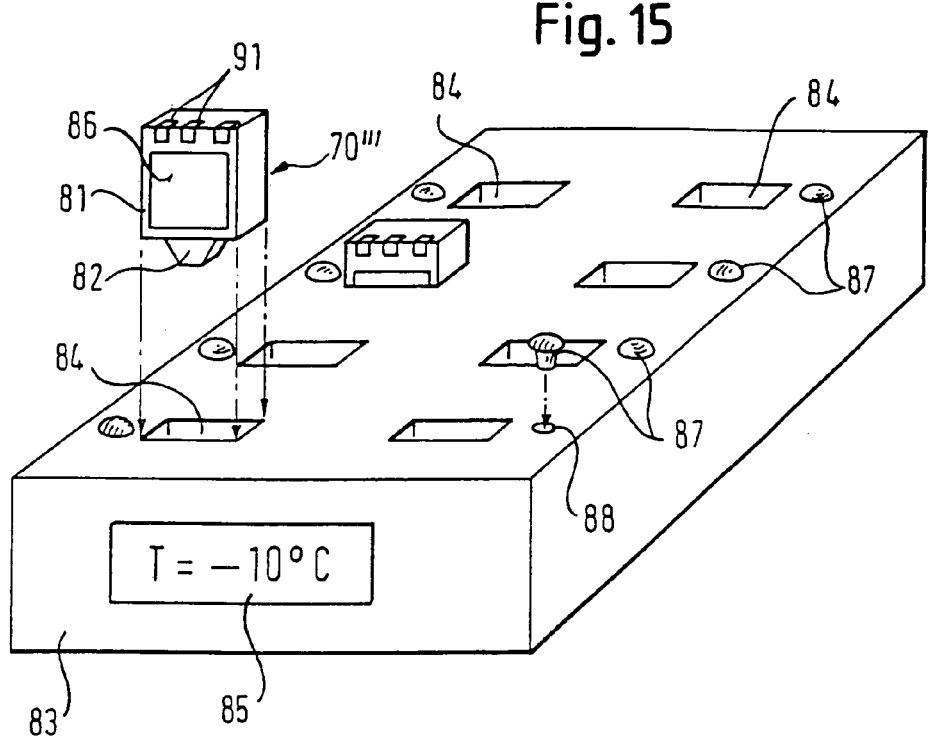
FIG. 15 shows a perspective view of a passive coolant carrier having fluid modules.

As shown in FIG. 15, several of such fluid modules 70'" are adapted to be slipped into a temperable carrier 83. This is of a box shape and has several seats 84 for fluid modules 70'" which are opened towards the upper surface and have a cross-section corresponding to the box-shaped part of shell 81. Seats 84 have a wall which tightly encloses the fluid modules 70'" which are inserted. The walls of seats 84 are surrounded by at least one cavity of carrier 83 into which a tempering liquid may be filled to form a cooling accumulator. The tempering liquid may be a brine. The salt concentration in the cooling accumulators may be adjusted depending on the temperature which is desired, which has an effect on the melting temperature. The concentration in the carrier shown has been adjusted so that the melting temperature is minus 10° C. to achieve an appropriate cooling of fluid modules 70'". The temperature adjusted is indicated on a label 85 which is adhered to the outside of carrier 83.

The fluid modules 70'" may be colour coded and/or have an inscription, for example on an outer surface 86. Appropriate coloured tabs or slip-on elements 87 may be disposed in suitable seats 88 or points next to seats 84 in which the appropriately coded fluid modules 70'" are or with which they are intended to be associated. This avoids confusions between various fluid modules 70'".

Such a tempering system may serve for keeping filled fluid modules 70'" in the laboratory refrigerator or at a workplace, and for transportation.

Figure 16:
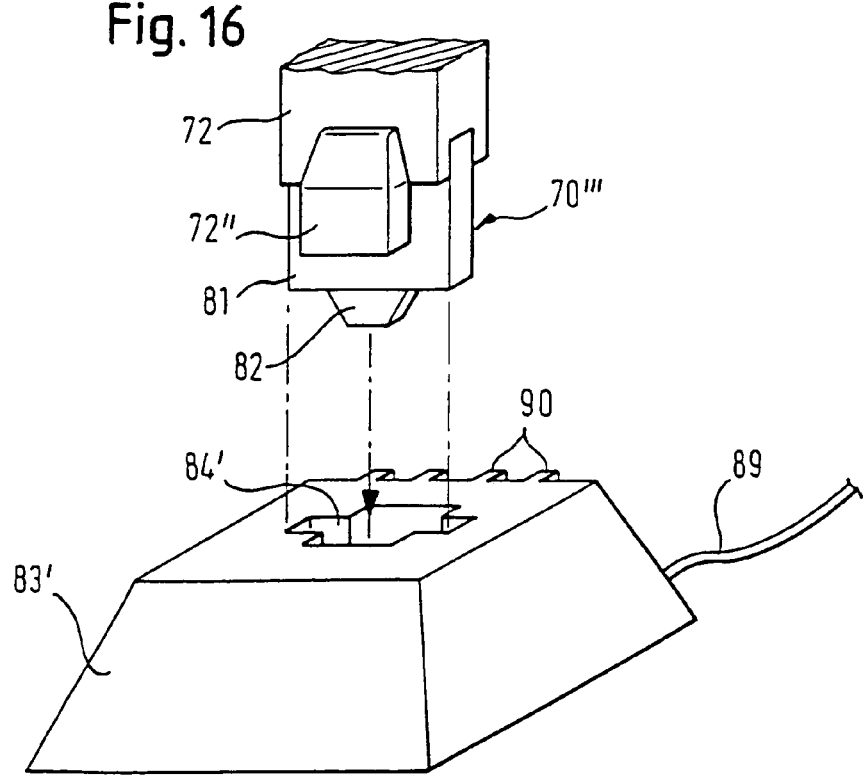
FIG. 16 shows a perspective view of an active coolant carrier having a fluid module ready for insertion in an actuating module.

As shown in FIG. 16, a fluid module 70'" has been slipped into an actuator module 72', from which it projects, however, unlike the one of FIG. 11. Fluid module 70'" is aligned on an actively tempered carrier 83'. This has a single seat 84' with a cross-section complementary to that of shell the 81 of the fluid module 70'" and a downwardly projecting shell portion 72" of actuator module 72' which will be referred to later in conjunction with FIG. 19. Carrier 83' may have Peltier elements to cool the fluid module 70'" in seat 84'. These are supplied with power via a connecting cable 89. Carrier 83' may have a cooling body 90 at the outside for the balance of temperature variations and for heat storage.

This cooling system is mainly suited for stationary disposal at a workplace. However, the cooling body 90 also favours its use for transportation and for being charged in a laboratory refrigerator.

The fluid module 70'" may be removed from the respective carrier 83 or 83' by slipping on the actuator module 72'.

Figure 17:
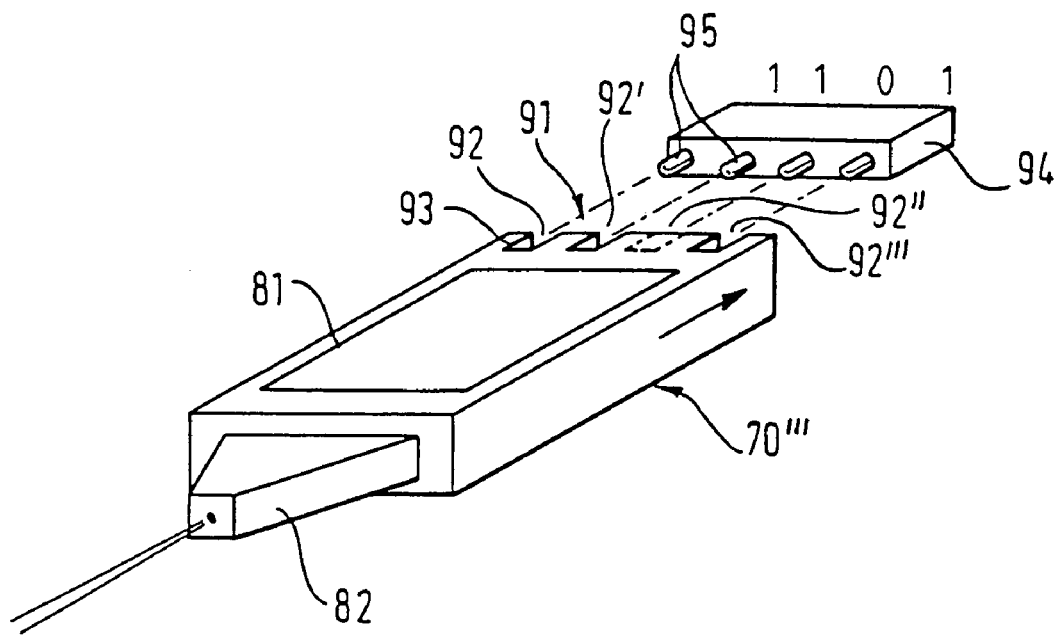
FIGS. 17 and 18 show a perspective front view of a fluid module including a coding and a sensing system aligned thereon (FIG. 17) and a perspective rear view of a fluid module portion including the coding unit (FIG. 18)
Figure 18:
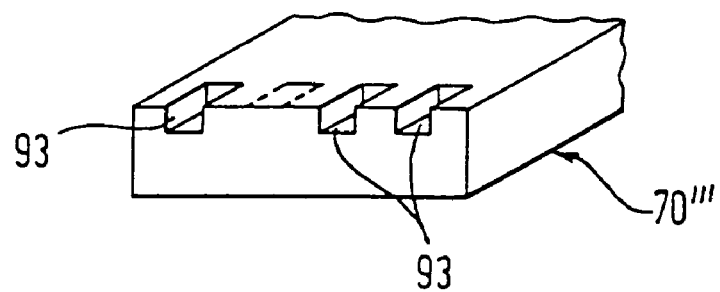

FIGS. 17 and 18 show a fluid module 70'" which has an encoding 91 on the shell 81 on an upper edge thereof; to be precise. Encoding 91 is formed by the existence of a depression 93 or of no depression in certain points 92, 92', 92", 92'".

For the lecture of encoding 91, an actuator module has a sensing device 94 with sensor pins 95 or other sensors which are able to detect the non-existence and/or existence of a depression 93 in places corresponding to the points 92, 92', 92", 92'". This enables the actuator module to detect the respective fluid module 70'" which is inserted.

FIG. 19 once more shows the lower part of the actuator module 72' with the fluid module 70'" inserted, which sets forth another particularity of this system. This is why actuator module 72', apart from having the projecting portion of fluid module 70'", has a forwardly and downwardly projecting shell portion 72", in which a laser diode 96 is disposed. This is aligned so as to designate the axis of motion and the point of impingement of the liquid dispensed from the fluid module 70'". As can be better seen in FIG. 20, the emission axis 98 of a laser diode 96 intersects the axis of motion 99 of the liquid exiting from the dispensing head 82 at an acute angle a for this purpose and is focussed on the intersection with the axis of motion. When a substrate 100 with its surface is accurately at the intersection the light beam 98 will exactly mark the point of impingement. When the position of substrate 100 deviates in a focussing range 101 around the intersection, the marking will merely shift, on the surface of the substrate, within a target range 102 which is very small because of the acute angle α.

The shell portion 72" may also accomodate a light-conducting fibre which aligns the light of a laser diode to the axis of emission 98.

FIG. 21 shows a proportioning chip 68" of an integrated light-conducting structure. The proportioning chip 68" is rectangular, but has a chamfered corner 103. There is a delivering means in the lower layer 104, which is an open-jet proportioner and, if need be, a micro-diaphragm pump formed in a semiconductor technology. This has its proportioning port in the lower portion 103' of the chamfered corner. The axis of motion 99' of the liquid jet is aligned perpendicularly to the chamfer of corner 103.

Disposed over the layer 104 is a glass layer 105 which is of a light-conducting structure. The light-conducting structure transmits light from an external light source 106, which is associated with one side of glass layer 105, to an upper portion 103" of the chamfered corner 103. A micromechanically manufactured lens 107 is integrated in the glass layer 105 there. The bundle of light exits perpendicularly to the chamfer of corner 103 along emission axis 98', which is parallel to the motion axis 99' of the liquid.

The outer surfaces of the glass layer may have a light-proof cover 108 to avoid losses of light.

Furthermore, a reservoir for liquid may be integrated in the layer 104 or 105. However, the reservoir may also be formed by an additional layer in a microsystem technology or may be superposed or externally disposed in a conventional construction.

The dispensing of liquid may additionally be indicated by a perceivable signal such an acoustic signal, a "flicker" of the light-beam pointer or merely by a marked pressure point of an actuator button.

What is claimed is:

1. A microproportioning system, comprising:
a reservoir;
a micro-diaphragm pump having an entrance connected to the reservoir;
a proportioning port connected to an exit of the micro-diaphragm pump;
a proportioning control means which is in an operative communication with the micro-diaphragm pump; and
common printed circuit board;
wherein the micro-diaphragm pump and the reservoir are combined to form one constructional element exchangeably connected to an actuator module in one of a microsystem technology and hybrid technology; and
wherein at least two components of the microproportioning system selected from the group consisting of proportioning controls means, a display, and an operating means are accommodated on the common printed-circuit board.

2. The system according to claim 1, wherein the printed-circuit board is disposed in a middle region of the actuator module.

3. A microproportioning system, comprising:
a reservoir;
a micro-diaphragm pump having an entrance connected to the reservoir;
a proportioning port connected to an exit of the micro-diaphragm pump;
a proportioning control means which is in an operative communication with the micro-diaphragm pump; and
an actuator module;
wherein the micro-diaphragm pump and the reservoir are combined to form one constructional element exchangeably connected to the actuator module in one of a microsystem technology and hybrid technology; and
wherein a power supply is accommodated in a head region of the actuator module.

4. A microproportioning system, comprising:
a reservoir;
a micro-diaphragm pump having an entrance connected to the reservoir;
a proportioning port connected to an exit of the micro-diaphragm pump; and
a proportioning control means operationally communicating with the micro-diaphragm pump for controlling operation of the micro-diaphragm pump in one of two opposite pumping directions to thereby control displacement of an auxiliary liquid column from the reservoir for suction of liquid through the proportioning port and an expulsion of liquid from the proportioning port;
wherein the proportioning control means controls a proportioned volume by controlling the displacement of the auxiliary liquid column along a distance between two sensors which are in an operative communication with the proportioning control means,
wherein the distance between the two sensors corresponds to the proportioned volume and is adjustable by one of manual adjustment and adjustment using a mechanical drive, and the two sensors detect meniscus of the auxiliary liquid column along a displacement length, and
wherein the mechanical drive includes a screw having a servo-drive and a screw nut, with one of the two sensors being mounted on the screw.

5. A microproportioning system, comprising:
a reservoir with a to-be-metered liquid;
a micro-diaphragm pump having an entrance connected to the reservoir;
an open jet proportioner having an entrance connected to an exit of the micro-diaphragm pump;
a proportioning port connected to an exit of the open jet proportioner; and
a proportioning control means operatively communicating with the micro-diaphragm pump and the open-jet proportioner,
wherein the reservoir is provided with at least one component of the microproportioning system selected from the group consisting of cooling means and a heat insulation for the to-be-metered liquid.

6. A microproportioning system, comprising:
a reservoir with a to-be-metered liquid;
a micro-diaphragm pump having an entrance connected to the reservoir;
an open jet proportioner having an entrance connected to an exit of the micro-diaphragm pump;
a proportioning port connected to an exit of the open jet proportioner;
a proportioning control means operatively communicating with the micro-diaphragm pump and the open-jet proportioner; and
a heating means provided at least in one of the components of the microproportioning system selected from the group consisting of the micro-diaphragm pump, the open jet proportioner, and connecting lines for heating the to-be-metered liquid.

7. A microproportioning system, comprising:
a reservoir with an auxiliary liquid;
a micro-diaphragm pump having an entrance connected to the reservoir;
a proportioning port connected to an exit of the micro-diaphragm pump; and
a proportioning control means operatively communicating with the micro-diaphragm pump for controlling displacement of an auxiliary liquid column from the reservoir for effecting one of suction of the liquid through the proportioning port and expulsion of liquid from the proportioning port by controlling an operation of the micro-diaphragm pump in one of a first direction in which the micro-diaphragm pump pumps the liquid from the reservoir and a second opposite direction in which the liquid is sucked into the reservoir, at least partially;

wherein the proportioning control means is adapted to control a volume being proportioned by controlling a stroke volume of the micro-diaphragm pump; and wherein the proportioning control means is adapted to determine the volume being proportioned on basis of calibration of the stroke volume that it establishes by displacing an auxiliary liquid column by the micro-diaphragm pump along with a calibration length between two sensors operatively connected with the proportioning control means for detection of meniscus of an auxiliary liquid column.

8. A microproportioning system comprising:
a reservoir with a to-be-metered liquid;
a micro-diaphragm pump having an entrance connected to the reservoir;
an open jet proportioner having an entrance connected to an exit of the micro-diaphragm pump;
a proportioning port connected to an exit of the open jet proportioner; and
a proportioning control means operatively communicating with the micro-diaphragm pump and the open-jet proportioner;
wherein the reservoir has a capillary balance system.

9. A microproportioning system comprising:
a reservoir with a to-be-metered liquid;
at least one system component selected from the group consisting of a micro-diaphragm pump having an entrance connectable to the reservoir, and an open jet proportioner having an entrance connectable to one of an exit of the micro-diaphragm pump and to the reservoir;
a proportioning port connected to an exit of the at least one of the micro-diaphragm pump and the open jet proportioner;
a proportioning control means operative by communicating with the at least one of the micro-diaphragm pump and the open jet proportioner;
wherein the reservoir and at least one of a micro-diaphragm pump and an open jet proportioner are combined to form one constructional element exchangeably connected to an actuator module in one of microsystem technology and hybrid technology; and
wherein the proportioning control means is connected to a sensor for detection of meniscus of the liquid at the beginning of a displacement length of the liquid for adjustment of an initial position for displacement of a liquid column.

10. The system according to claim 9, wherein the sensor is associated with a dispensing tube for the liquid.

11. The system according to claim 10, wherein the dispensing tube is connected to a constructional element.

12. The system according to claim 11, wherein the constructional element is exchangeably connected to a base region of an actuator module.

13. The system according to claim 12, wherein the proportioning control means is permanently connected to the actuator module, and the constructional element is separably connected to the proportioning control means by an electric contact.

14. The system according to claim 12, wherein a sensor is permanently connected to the actuator module.

15. The system according to claim 12, wherein a power supply is accommodated in a head region of the actuator module.

16. A microproportioning system comprising:
a reservoir with a to-be-metered liquid;
at least one system component selected from the group consisting of a micro-diaphragm pump having an entrance connectable to the reservoir, and an open jet proportioner having an entrance connectable to one of an exit of the micro-diaphragm pump and the reservoir;
a proportioning port connected to an exit of the at least one of the micro-diaphragm pump and the open jet proportioner;
a proportioning control means operative by communicating with the at least one of the micro-diaphragm pump and the open jet proportioner;
a common printed circuit board; and
an actuator module;
wherein the reservoir and at least one of a micro-diaphragm pump and an open jet proportioner are combined to form one constructional element exchangeably connected to the actuator module in one of microsystem technology and hybrid technology; and
wherein at least one system component selected from the group comprising the proportioning control means, display, and operating means is accommodated on the common printed-circuit board.

17. A microproportioning system, comprising:
a reservoir with an auxiliary liquid;
a micro-diaphragm pump having an entrance connected to the reservoir;
a proportioning port connected to an exit of the micro-diaphragm pump; and
a proportioning control means operatively communicating with the micro-diaphragm pump for controlling displacement of an auxiliary liquid column from the reservoir for effecting one of suction of the liquid through the proportioning port and expulsion of liquid from the proportioning port by controlling an operation of the micro-diaphragm pump in one of a first direction in which the micro-diaphragm pump pumps the liquid from the reservoir and a second opposite direction in which the liquid is sucked in the reservoir, at least partially;
wherein the proportioning control means is connected to sensors for detection of meniscus of the liquid at beginning of a displacement length of the liquid for adjustment of an initial position for displacement of an auxiliary liquid column.

* * * * *